United States Patent
Melby et al.

(10) Patent No.: US 9,147,043 B2
(45) Date of Patent: Sep. 29, 2015

(54) MEDICAL DISPENDING SAFETY SYSTEM THAT MONITORS DRUG INGESTION

(71) Applicants: Doug Melby, Bainbridge Island, WA (US); David G. Greenberg, Phoenix, AZ (US)

(72) Inventors: Doug Melby, Bainbridge Island, WA (US); David G. Greenberg, Phoenix, AZ (US)

(*) Notice: Subject to any disclaimer, the term of this patent is extended or adjusted under 35 U.S.C. 154(b) by 197 days.

(21) Appl. No.: 13/921,126

(22) Filed: Jun. 18, 2013

(65) Prior Publication Data
US 2014/0156065 A1 Jun. 5, 2014

Related U.S. Application Data

(60) Provisional application No. 61/660,990, filed on Jun. 18, 2012.

(51) Int. Cl.
*G08B 21/00* (2006.01)
*G06F 19/00* (2011.01)

(52) U.S. Cl.
CPC .................. *G06F 19/3462* (2013.01)

(58) Field of Classification Search
CPC .................................. G06F 19/3462
USPC .............. 340/573.1, 309.16, 539.2; 600/300, 600/301; 705/2, 3
See application file for complete search history.

(56) References Cited

U.S. PATENT DOCUMENTS

2010/0228566 A1* 9/2010 Taylor et al. ................ 705/3

* cited by examiner

*Primary Examiner* — Jeffery Hofsass
(74) *Attorney, Agent, or Firm* — Olympic Patent Works PLLC (57) ABSTRACT

The current application is directed to methods for assessing patient risk and managing chronic pain patients in order to improve functional outcomes, decrease mortality and morbidity, and to emphasize the cost effectiveness of chronic pain treatment. Nurse case managers working with physician consultants who have experience in dealing with complex noncancerous chronic pain diagnoses, substance abuse, mental health conditions, and drug diversion are employed. Chronic pain case management services may be employed, often along with specialized drug-dispensing devices.

1 Claim, 6 Drawing Sheets

MEDICAL DISPENSING SAFETY SYSTEM THAT MONITORS DRUG INGESTION

CROSS-REFERENCE TO RELATED APPLICATION

This application claims the benefit of Provisional Application No. 61/660,990, filed Jun. 18, 2012.

TECHNICAL FIELD

The present invention is related to drug delivery and drug monitoring systems.

BACKGROUND

Most nurse practitioners, physician assistants, and physician prescribers of chronic pain opiate drugs do not have any formal training in the diagnosis, treatment, or safe medication management and monitoring for patients on high dosage narcotic preparations. Many chronic pain specialists often do not even own a comprehensive textbook on chronic pain medicine. Their practices are often quite limited in scope and consist simply of prescribing patients the opioid drugs they request. These chronic pain specialists often have minimal knowledge of relevant anatomy, physiology, pharmacology, mental health, substance abuse, and drug-diversion-related issues. Verifiable functional improvement in their patients is limited and many of their patients have no true improvements in their medical, occupational, or social lives with treatments that often consist solely of high-dosage narcotic regimens. Further complicating matters is the fact that a disproportionately high number of patients in these practices are involved in substance abuse and/or commercial drug diversion activities, along with having high rates of accidental overdose death and criminal commercial drug diversion activities.

On the other hand, there are a growing number of highly trained interventional chronic pain specialists with fellowship training in performing invasive chronic pain procedures. Unfortunately, a very large percentage of invasive chronic non-cancerous pain treatment procedures have never been scientifically proven to be any more effective than placebos. Complicating matters is the fact that many of these procedures are not inexpensive. These well-trained interventionists often recommend expensive unproven procedures as the mainstay of chronic non-cancerous chronic pain treatment and then delegate narcotic and other controlled substance prescribing to employed and/or contracted midlevel providers that may have their own DEA licenses, but who have no formal training or certification in chronic pain management or addiction medicine/mental health.

Safety measures for prescription opioids and other controlled substances that would help address epidemic-level drug-related problems, including death from accidental overdose, brain damage, drug DUI and motor vehicle accidents, and massive criminal controlled substance drug diversion activities in the that supply the major gateway drugs leading to drug addiction, are becoming an area of research and development interest. Drug overdose has become the number one cause of accidental death in the USA. Our country is currently experiencing an ever-growing epidemic of accidental deaths due to $R_x$ drug overdose, and most of these deaths involve narcotic (opioid) pain pills. The CDC has declared this $R_x$ poisoning epidemic to be a national healthcare emergency and it involves persons who ingest narcotic pain pills for the purposes of pain control and/or recreational use. Tragically, many accidental narcotic overdose victims do not die, but rather suffer severe permanent brain damage as a result of the respiratory depression produced by toxic doses of narcotics. The excess costs to the healthcare system and society caused by minimally controlled $R_x$ drug abuse and drug diversion are in the hundreds of billions of dollars per year. One of the major contributing factors to this problem is that most opioid prescribing nurses, physicians, and PAs normally write prescriptions for 30-day (or longer) supplies of pain medicines to patients who are at elevated risk for accidental overdose, drug abuse, and/or commercial drug diversion. Too many patients receive large monthly supplies of powerful narcotic drugs and then either take toxic doses of these pills or sell these pills to criminal commercial drug dealers for a large profit. As a result, wrongful death lawsuits against prescribing nurses, physician assistants, and physicians are on the rise. More importantly, the current situation has caused tragedy for hundreds of thousands of U.S. families.

One example of commercial drug diversion is a patient who pretends to have a painful condition and gets a careless medical provider to prescribe oxycontin 80 mg tablets three times per day. This equals 240 mg of oxycodone per day or 7,200 mg per month. The average price for illicit oxycodone in many locales is $1/mg, which means that the commercial drug diverter can easily make over $4,000 per month tax free on each $R_x$. Many diverters see half a dozen careless providers each month and are able to net over $20,000 per month tax free. Drug diversion is especially prevalent in the Medicare and Medicaid patient populations, which means that taxpayers are directly subsidizing criminal diversion rings and heroin producers and heroin dealers. To date, law enforcement has been unable to curtail the rapidly growing business of commercial drug diversion in the USA. In short, criminal commercial diversion is so widespread because it is such an easy way to make huge amounts of tax-free dollars. Law enforcement cannot even begin to control the problem. Medical and mid-level regulatory boards are also unable to effectively deal with this problem because their investigative budgets have been greatly reduced and many simply do not have enough qualified investigators. Meanwhile, intensive lobbying efforts by the pharmaceutical industry and the "grassroots" pain patient advocacy that they heavily fund have had a chilling effect on the development of effective mandatory counter diversion measures in the U.S. Some conscientious narcotic drug prescribers try to utilize controlled substance $R_x$'s with smaller numbers of pills for their high-risk patients in order to increase patient and societal safety; however, this requires patients to go to both the doctor's office and the pharmacy every few days and this causes difficulties for patients insofar as transportation and co-payments to doctors and pharmacists.

Methadone clinics also have serious problems with patient drug abuse, overdose and commercial diversion, in that they normally allow compliant patients to stop coming to the clinic every morning to get their daily dose of this narcotic maintenance drug. These reliable patients are then given week-long or even multiple week supplies of bulk liquid methadone that is often implicated in accidental drug overdoses and/or criminal commercial drug diversion. Many methadone clinics have grossly inadequate anti-diversion policies and procedures. Finally, children depend upon criminals that commercially divert narcotic pain drugs to fuel their own drug abuse, addiction, and overdose tragedies. This is because 15-year-olds cannot obtain powerful narcotic prescriptions from physicians or nurses without the written consent of their parents, and most parents will not consent to their 14-year-olds being placed on long-term high-dose narcotic drug regimens for relatively minor conditions, as is the case for many adults. A 14-year-old might be able to sneak a bit of opioid drugs from his or her parent's medicine chest, but to become addicted to opiates, humans normally must ingest high doses of narcotic drugs for a couple of months. There simply are not enough powerful narcotic drugs to become addicted to in the typical family's medicine chest. However, young people do sometimes accidently overdose and die by ingesting unsecured narcotics and other controlled substances from the family medicine cabinet.

Studies of young heroin addicts in the USA reveal that the majority of them first became addicted to $R_x$ pain pills and then were switched to cheaper heroin by their drug dealers when they could no longer afford to buy the more expensive diverted pain pills. Today, thanks to uncontrolled diversion of opioid/narcotic drugs, we have the largest heroin addiction epidemic among young people in our country's history. Most of the growth in criminal-drug-diversion-related youth heroin addiction appears to be in the Caucasian population.

SUMMARY

The current application is directed to methods for assessing patient risk and managing chronic pain patients in order to improve functional outcomes, decrease mortality and morbidity, and to emphasize the cost effectiveness of chronic pain treatment. Nurse case managers working with physician consultants who have experience in dealing with complex non-cancerous chronic pain diagnoses, substance abuse, mental health conditions, and drug diversion are employed. Chronic pain case management services may be employed, often along with specialized drug-dispensing devices.

BRIEF DESCRIPTION OF THE DRAWINGS

FIG. 1 depicts the visible components of the drug-dispensing device that a user responds to or interacts with.

DETAILED DESCRIPTION

Ethical chronic pain practitioners spend a significant portion of their work days in $R_x$ safety activities that are essential to decrease drug abuse, drug diversion, and abuse-related mortality and morbidity. These activities include: (1) reviewing their patients' past medical records, screening patients for risk factors that include a complete mental health, substance use, and family history, along with the administration of various opioid risk screening tests; (2) checking the state controlled substance prescription monitoring database; (3) utilization of urine drug screening testing; (4) utilization of random pill counts; (5) utilizing and explaining a comprehensive informed consent processes that include information about drug addiction, overdose death, and other serious complications of opioid and other controlled substance prescribing; (6) utilizing, explaining, and appropriately enforcing a comprehensive chronic opioid treatment agreement; (7) dealing with high-risk patients and non-compliant patients who have violated the terms of their treatment agreements. When performed, the above safety-related activities take up approximately 2-3 hours of provider time per day, in a hypothetical outpatient pain practice that sees eight new patients and 30 follow-up patients per day. Additionally, the practice's office support staff spend a total of about 6-8 hours per day in the $R_x$ safety activities noted in items 1-7 above.

Non-ethical pain-pill mill providers who do not engage in the above activities have a competitive advantage over the ethical prescribers, as they can see significantly more patients per day and spend less on office staff wages and other expenses. Furthermore, drug abusers and commercial drug diversion rings strongly prefer to patronize chronic pain specialists who operate pill mills and who do not utilize $R_x$ safety-related procedures. Finally, the above $R_x$ safety procedures are only indirect measures. They do not in any real way prevent drug abuse and drug diversion, they simply make it somewhat more cumbersome for drug abusers and commercial drug diverters to operate.

The currently disclosed methods and systems directly prevent drug abuse and diversion. Furthermore, these methods and systems level the playing field between ethical and non-ethical providers by removing activities that place ethical pain drug prescribers at an economic disadvantage to the high volume pill-mill prescribers. Using the currently disclosed methods and systems, ethical chronic pain specialists no longer serve as policemen for their patients, and instead spend more of their time in better diagnosing and treating them. Additionally, the currently disclosed methods and systems further save money by reducing the need for expensive urine drug screening, as the control over the controlled substances is far more direct and effective.

As opposed to pills, liquid and/or orally dissolving thin film medications are far more difficult to divert and abuse in a system that documents proper drug ingestion. For example, when a patient is being observed ingesting a pill, the observer can be fooled via the following methods: (1) the patient can cheek the pill by hiding it between his or her cheek and gums; (2) the patient can "tongue" the pill by hiding it under the base of his or her tongue; and (3) the patient can actually swallow the pill and then, immediately after visual inspection, vomit the pill back up and retrieve it. By utilizing the currently disclosed methods to defeat proper pill ingestion, the patient is now free to: (a) crush the pill and snort it; (b) chew the pill and swallow it; (c) cook the pill with water and inject it; (d) hoard the pills so as to take a much larger abusable dose of medicine at a later time; (e) divert the pills to friends or family; or (f) sell the pill to a commercial drug diversion ring.

In contrast, when a patient swallows 6-8 ounces of a dilute liquid preparation and then opens their mouth for a visual inspection followed by speaking a few sentences, it is virtually impossible to hide the 6-8 ounces of liquid anywhere in their mouth. Furthermore, when the patient swallows the liquid and then vomits it back up, an emesis of a very dilute solution of the drug that is contaminated by stomach acid, other gastric secretions, and partially digested food particles is produced. This diluted liquid would have an extremely limited value in casual or commercial drug diversion applications.

The currently disclosed methods and systems for securing, documenting and accounting for the final disposition of controlled substances and other medications make it dramatically more difficult for high-risk patients to abuse and/or divert their prescription drugs. The currently disclosed methods and systems provide a practical solution that can help the field of medicine protect pain patients, children, and society from the harms caused by prescription narcotic drug abuse, overdose, and drug diversion. Furthermore, the currently disclosed methods and systems also protects prescribing pain physicians, primary care doctors, health care insurers, and other providers who treat chronic pain patients.

The currently disclosed methods and systems are specifically designed to prevent: (1) narcotic and other controlled $R_x$ drug abuse; (2) narcotic and other controlled drug addiction; (3) overdose deaths; (4) overdose brain damage; (5) criminal commercial drug diversion; (6) drug DUI arrests and drug-caused traffic and workplace accidents; (7) wrongful death and injury lawsuits against physicians, pharmacists, nurses, PAs, health insurance companies, and pharmaceutical companies; and (8) non-employability due to the negative effects of controlled drugs on behavior and cognition. The currently disclosed methods and systems also decrease the amount of new young heroin addicts who switch to heroin when they can no longer afford to buy criminally diverted pain pills. In time, this decreases some of the criminality, prostitution, violence, trauma, overdose, and diseases that are major components of the heroin addict's daily activities. Eventually, as current heroin users die off, and with the generation of fewer new heroin users, the rates of HIV, MRSA, and Hepatitis C infection will also decrease with implementation of the currently disclosed methods and systems. Also, the currently disclosed methods and systems are utilized to prevent abuse and diversion of other controlled $R_x$ drugs such as amphetamines, benzodiazepines, and sleep medications.

The currently disclosed methods and systems (a) control and monitor the controlled substance use from the moment the high risk patient picks up his or her controlled substance prescription; (b) decrease drug abuse and drug addiction; (c) decrease drug diversion; (d) decrease the adverse health, social, legal/criminal, and economic consequences of drug abuse/addiction in our society; (e) largely eliminate the most common gateway to heroin addiction in the USA, thus decreasing the creation of new young heroin addicts; (f) free up more time for ethical narcotic prescribing providers, who are currently having to spend large amounts of time/money attempting to prevent drug abuse and diversion; (g) decrease the negative impact of careless "pill mill" types of prescribers; currently have on our society; and (h) dramatically decrease the amount of money and time spent on collecting, transporting, testing, interpreting and dealing with non-compliant patients, via the current widespread use of easily defeated expensive urine drug-screening panels.

The currently disclosed methods and systems are designed to deliver and document that the patient is both dispensed and then ingests the appropriate doses of opioid pain medicines only at those times prescribed by the patient's doctor while, at the same time, dramatically decreasing commercial drug diversion activities. The currently disclosed methods and systems utilize a secure liquid and/or orally dissolving thin film medication dispensing unit that meters out the patient's prescribed dose of medication at the correct times during the day. The liquid medicine is dispensed into a six-ounce glass of water and the patient then drinks the glass of water with the medication in it. Orally dissolving thin film medication is delivered to the patient on a stick that is held in the patient's mouth until the film has dissolved. Confirmation that the actual patient has swallowed his medication is done by variable combinations including utilizing fingerprint recognition, facial recognition, voice recognition, and iris/retinal scanning.

Current drug dispensing problems include: (1) Law enforcement is overwhelmed by the sheer volume of $R_x$ drug abuse and commercial drug diversion. When they do investigate, they naturally often focus more on reactive cases involving multiple patient deaths, not proactive measures to prevent diversion or abuse; (2) Medical and nursing regulatory boards often do not have the will or the properly trained investigative staff to investigate the sheer numbers of problem controlled substance prescribers; (3) Although many excellent national guidelines exist to assist physicians in decreasing $R_x$ drug abuse and diversion, they are not mandatory. Most controlled substance prescribing doctors, nurses and PAs ignore these excellent guidelines because they add 15 minutes of uncompensated time to each patient visit and this lost time equals lost provider income; (4) Most providers that $R_x$ pain meds do not check their state's controlled substance $R_x$ databases; again, because this is not mandatory and takes five more minutes of time and reduces provider income. PMP programs are easily defeated by drug diverters and drug abusers who use false ID cards; (5) Most providers that prescribe controlled substances do not perform random urine or hair drug testing on their patients as this also takes precious time and erodes provider profits. Smart abusing/drug diverting patients prefer to patronize the majority of medical and nursing practices that do not utilize drug testing; (6) Most providers and pharmacies do not scrutinize patient identification cards such as drivers licenses and when they do look at ids, they are easily fooled by amateur ID forgeries. Doctor shopping is very easy with cheaply available false ID cards; (7) Most providers that prescribe controlled pain medicines do not perform random pill counts on their patients. Counting pills and then dealing with non-reconcilable counts takes time and hurts provider profitability. Even if they are randomly called to submit to pill counts, abusers and diverters can always buy or rent pills to bring to their pill count session; (8) Most providers that prescribe controlled pain medicines do not obtain and properly review old medical records from their patient's previous treating providers, because this takes provider and staff time and therefore erodes profits; (9) Most providers that prescribe controlled pain medicines do not perform an adequate informed consent with their patients that mentions overdose death, addiction risk, car accidents, addicted newborns, etc., as this practice also takes time and decreases profits; (10) Most providers that prescribe controlled pain meds either do not use a written controlled substance treatment contract/agreement, or they fail to enforce such an agreement when the patient violates the terms and has a urine test positive for drugs obtained from sources other than the doctor named in the contract/agreement, or does not have the prescribed controlled drug in their urine; (11) Most providers of chronic pain controlled substances do not evaluate their patients for risk of drug abuse or diversion, even though all reputable authorities strongly recommend that this be done for every pain patient prior to prescribing controlled substances; (12) Most providers of chronic pain controlled substances do not take adequate substance abuse or mental health histories on their patients and do not examine their patients for signs of substance abuse; and (13) The state controlled substance prescription monitoring programs are only for a particular state, and they all operate in different manners re: drugs they monitor, reporting times, the time it takes for a provider to get a requested patient's report, as well as who has access to such records. Also, drug abusers and diverters can easily defeat monitoring programs by hitting several different states whose $R_x$ monitoring programs do not communicate with other states.

In summary, the current state of affairs is that pain $R_x$ing providers, law enforcement personnel, regulatory agencies, medical boards, pharmacists, politicians, and narcotic manufacturers have directly and not infrequently intentionally failed to control prescription drug abuse/addiction and drug diversion in the USA. In doing so, a perfect storm has been created for children to easily obtain commercially diverted controlled pain medications, become addicted to them, and then switch to low cost heroin from Mexico and Afghanistan when they can no longer afford to buy diverted pain pills.

Approximately 40 states have prescription monitoring programs (PMPs) and their role is to reduce drug abuse and drug diversion by allowing prescribing providers to query the database to find out whether their patients are obtaining controlled substances from multiple physicians, nurses, PAs, dentists, or other providers. Each of the 40 participating state PMPs does not routinely initiate communication of potentially lifesaving data with the other 40 state programs or with involved prescribing providers. The state PMPs are predominately passive repositories of stored controlled prescription data.

These programs are all designed, implemented, and run by the individual states, and they have differences in the types of $R_x$ data they collect and store, as well as in when and who they will release information to, and what data they will actually release. None of the state databases function to warn prescribers in a real-time proactive mode that could have a positive effect on patient safety. They are simultaneously both minimally reactive and passive systems that do not reach out to doctors and other prescribing providers in real time in order to attempt to save lives or prevent criminal commercial drug diversion.

Most importantly, PMPs fail to adequately protect patients and the general public because they depend upon voluntary cooperation by the prescribing providers, and the overwhelming majority of controlled substance prescribers in almost all states refuse to query their state PMP databases for information concerning their patients. In short, the vast majority of prescribing providers do not want to obtain PMP database information, as this costs them time and money and also forces a modicum of both liability and accountability upon controlled substance prescribers. Furthermore, current state PMPs also are routinely defeated by drug abusers and commercial drug diverters who use fake ids at their doctor's offices and pharmacies. Medical providers and pharmacists are unskilled at being able to detect false patient ids. None of the state PMPs demand that every pharmacy patient produce proper ID before being allowed to pick up any controlled substance $R_x$. PMPs are also often easily defeated by drug abusers and commercial diverters utilizing pharmacies in multiple different states that do not communicate with each other.

The currently disclosed methods and system include a national PMP database that (1) collects prescribing data for all 50 states and U.S. Territories covering all legal controlled substances, and does not simply involve a limited number of substances or jurisdictions; (2) allows and actively promotes free communication and proactive data sharing across state and territorial borders; (3) routinely feeds critical electronic prescribing data to the appropriate prescribing providers regarding their patients' full controlled substance prescription history, transmits updates to providers every 24 hours, the information immediately appearing on each patient's electronic medical records, the providers' emails, and via voice mail message and text messaging. Providers no longer need to spend time to query the system for each and every patient. They will automatically receive timely and potentially lifesaving controlled substance prescribing information as it becomes available. This will translate into less criminal commercial drug diversion, less drug abuse/addiction, less $R_x$ overdose death, fewer drug impaired drivers causing serious MVAs, and in time, lower rates of young persons becoming addicted to heroin. Prescribing providers who ignore MSS PMP reports will do so at both their patients' and their own peril. In short, the national PMP database forces prescribers of controlled substances to become more accountable to the safety needs of their patients and society at large; and (4) utilize positive patient identification procedures to include biometric data such as a thumbprint, iris/retinal scans, and/or or a voice print in addition to a picture ID and/or a pin number to verify patient ids at the time they pick up their prescriptions.

Examples of sample proactive MSS reports and MSS safety tips that will accompany such reports:

A. Dec. 1, 2012: Doctor Chester Harold Anderson, D.O.—"Your patient Selena Marie Sepulveda has obtained oxycodone 30 mg tablets from three other providers in the last 24 hours. It is strongly suggested that you contact her immediately as she is at increased risk of overdose death and/or criminal drug diversion."

B. Aug. 14, 2013: Nurse Practitioner Hortensia Smith Wilson—"Your patient George Armstrong Custer, Sr. has obtained Ambien and Xanax prescriptions from two other providers today, along with also obtaining prescriptions for fentanyl lozenges and fentanyl patches from two other additional providers. It is strongly suggested that you contact him immediately as he is at increased risk for overdose death and/or criminal drug diversion."

Prior and current art state run PMPs have failed reduce in criminal drug diversion, heroin addiction in children, or overdose death, due to their above documented inherent deficiencies. The currently disclosed national database PMP protects people and children in ways that the voluntary, passive, and poorly designed, state PMPs fail to. The national PMP database utilizes existing customer service software programs along with innovative original algorithms that are custom developed to facilitate public health and promote enhanced protection of the population from the current epidemic of inappropriate controlled substance prescribing.

The purposes of medication safety system's method and device patents are to significantly decrease drug abuse, overdose death, health care costs, and criminal commercial controlled substance diversion. The currently disclosed devices and methods are used to increase the safety of controlled substance prescribing to individuals who with known histories of substance abuse, drug diversion, drug dealing, and non-compliance with physicians' instructions and treatment agreements.

Not every non-cancerous chronic patient who receives controlled substances needs to utilize the currently disclosed device. However, each and every chronic pain patient who receives chronic opioid (narcotic) prescriptions should to be assessed for their risks of substance abuse, accidental overdose death, drug diversion, and drug related DUI. (see both the current American Pain Society's and the American Academy of Pain Medicine's guidelines re: the duty of prescribing pain providers to assess patient risk.) Unfortunately, the majority of providers who $R_x$ opioid and other controlled substances to pain patients do not properly assess patient risks for the aforementioned aberrant behaviors. The currently disclosed methods and systems provide a rational and fair risk assessment service for chronic pain patients that will utilize elements of the below patient inclusion criteria, along with checking for any past substance abuse related problems involving the criminal justice system.

The high-risk patient inclusion criteria (each patient is assessed individually, and the patient's current status findings are more important than historical information from the distant past) include the following:

(1) Patient's past medical history—substance abuse, addiction, ongoing tobacco use, history of DUI, probation, or other arrest/jail/probation in any way related to substance abuse, history of substance abuse treatment or 12-step meeting attendance, anxiety, depression, current use of benzodiazepines, controlled sleeping medications, anti-depressants, $R_x$ stimulant drugs, marijuana, other illicit drugs or carisprodol, current use of multiple opioid drugs, current narcotic drugs from multiple different providers, psychiatric treatment, major trauma in any way related to substance use, hepatitis C, hepatitis B, HIV, overdose on any meds, recreational drugs or alcohol, history of blackouts on any substances, use of any alcohol while on controlled substances or anti-depressant medications, ever attempted suicide, ever fired from a medical practice for non-compliance, any use of alcohol that the patient refuses to stop if $R_x$d controlled substance, controlled drugs, illicit drugs, or tobacco while pregnant, multiple non-communicating health care providers prescribing controlled substances during any given year, borderline personality disorder or cluster B traits, any lifetime use of illicit or prescription drugs by injection, currently on extremely high doses of controlled substances, history of sexual abuse, other PTSD.

(2) Family history—substance abuse or alcohol problems of any kind, depression, anxiety, psychiatric hospitalization, arrest/jail sentence for substance related problems, history of substance abuse treatment, premature death related to substance abuse of any kind, suicide or suicide attempt, use of alcohol, controlled drugs, illicit drugs, or tobacco while pregnant, history of chronic pain condition and currently using $R_x$ controlled substances, any drug overdose history, current tobacco use, ever fired from a medical practice for non-compliance.

(3) Social history—any job loss or failure to gain employment related to any form of substance abuse, loss of important relationships due to substance abuse, financial problems due to substance abuse, discharged from military related to substance abuse, loss of hobbies and/or previously enjoyable activities in any way related to substance abuse.

Figure 1:
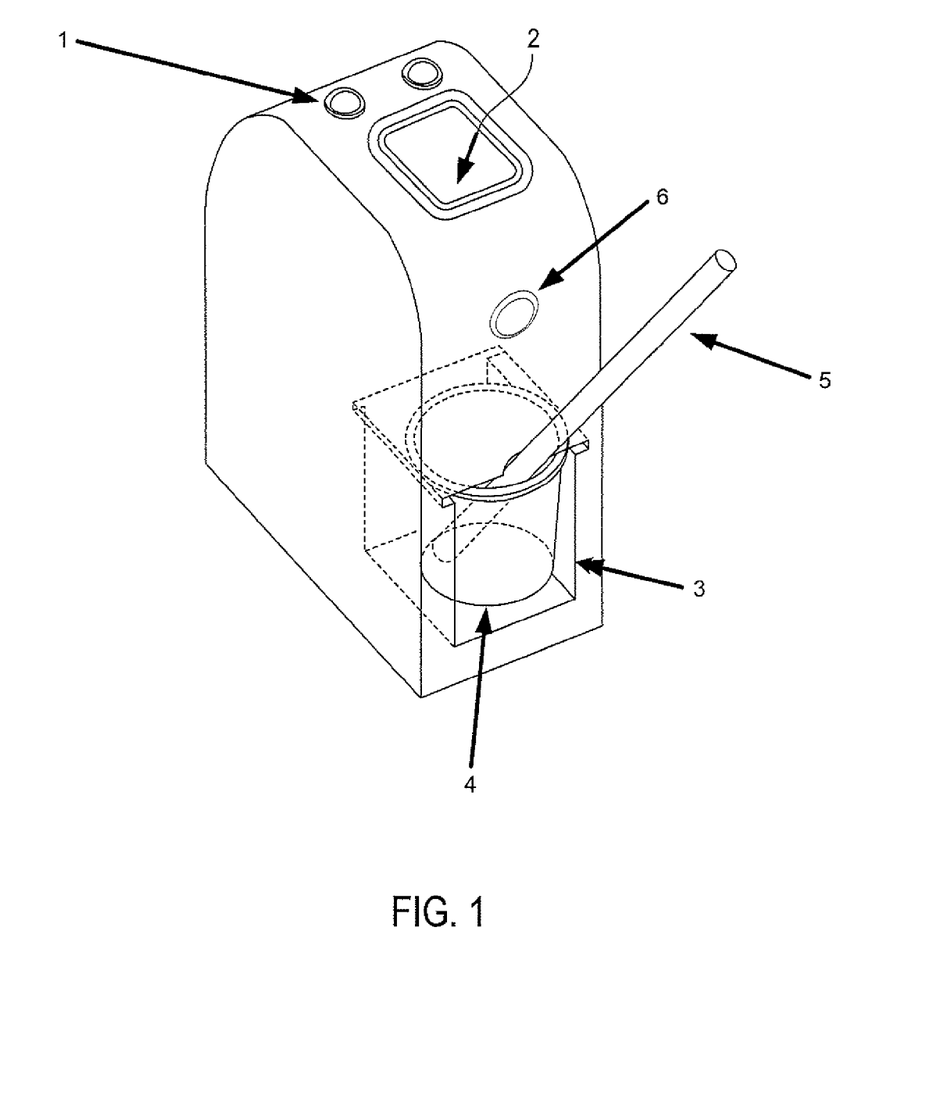

The current application discloses a drug-dispensing device. FIG. 1 depicts the visible components of the drug-dispensing device that a user responds to or interacts with. First, the patient sees alarm/alert lights (1) blinking (yellow) to announce the device is ready to dispense the next dose. The user then places his or her thumb on the thumbprint reader (2) to authenticate his or her identity (users furnish thumbprints and photo at pharmacy). Alert/alarm lights (1 then blink (green) with positive authentication and signal the user to place a provided cup (4) into opening (3). Medicine is then be dispensed into cup (4) for ingestion through the provided straw (5). The provided straw (5) is of a length that places the user's face in position to be filmed by the onboard camera (6).

Figure 2:
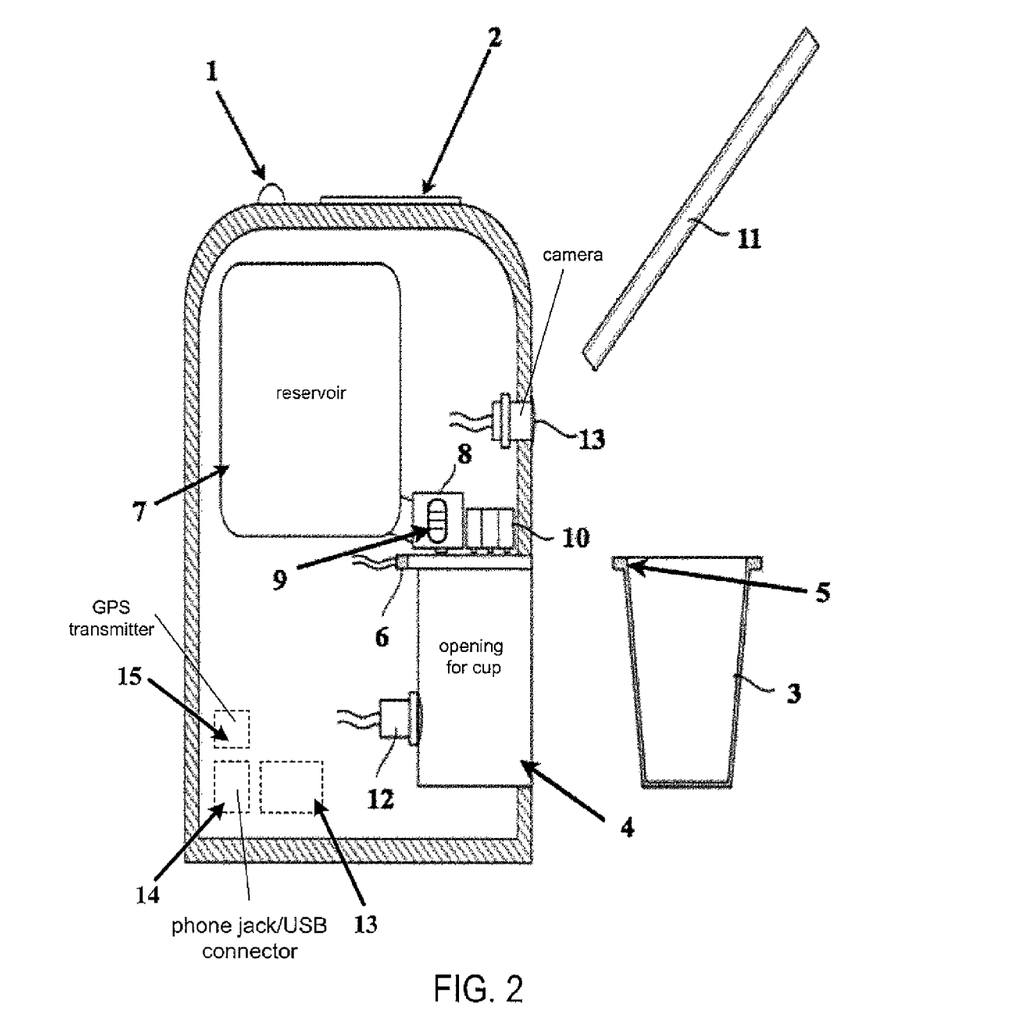
FIG. 2 is side view of the liquid dispensing device with all components labeled.

FIG. 2 shows the internal and external components of the drug-dispensing device. In use, alarm/alert lights (1) function to signal the user that his or her next dose is available (per instruction prescribed by physician and downloaded to device's CPU (13) and that the patient can now initiate the sequence by placing his or her thumb on the thumbprint reader (2) to authenticate his or her identity. Alarm/alert lights (1) will then signal positive ID (blinking green) (or negative ID blinking red) which will then allow (blinking green) the user to place the provided cup (3) into the opening (4). Negative ID causes device to suspend operation. The cup must be pushed completely into the opening (4) so the upper lip of the cup (5) makes and maintains contact with the sensor (6). When sensor (6) detects proper cup (3) placement, medication is transferred from the reservoir (7) to the medication dispenser (8) where user can confirm the correct dose amount through the measured "sight glass" (9). User conforms correct dose by again placing his or her thumb on thumb print reader (2) to continue with dispensing of medicine into cup (3). While medicine is being dispensed into cup (3), a randomly selected color is created by injecting dye into the medicine being dispensed into cup (3) from the dye injectors (10). When all medicine has been dispensed into cup (3), user pushes his or her provided straw (11) through the slot above the cup (3) and begins ingesting medicine. All medicine must be ingested, as seen by the lower camera (12) to meet the compliance standards. The provided straw (11) is measured to insure user is seen by upper camera (13) which also registers color of medicine being ingested through the clear straw (11).

Prior to the operations described above, the device must be initiated by the user at his or her residence. After receiving the device from a pharmacy (where prescription instructions, thumbprint scan and user photo and user home address have been loaded into device CPU (13), the user takes the device to his or her home and either plugs the device into a phone jack/USB connector (14) or connects to his or her WiFi network to establish connection to a web server managing all such devices. Simultaneously, the onboard GPS transmitter (15) sends location information that must match the address listed as the home residence of user where the device is expected to be used. With a GPS match and connection to the managing server confirmed, alarm/alert lights (1) flash to indicate the user should place a thumb on the thumb print reader (2) to complete the initialization process is complete and that the device is now ready for use.

Compliance and monitoring of patient is done by:
(a) thumbprint authentication (2) for initiating the dosing process;
(b) GPS location and patient address match for device operations;
(c) doses being available only at times prescribed (instructions loaded onto device CPU);
(d) medication dispensed into monitored cup (3)
    (d1) cup position is confirmed by sensor (6) before medication is dispensed,
    (d2) color added to medication by dye injectors (10),
    (d3) color of medication in cup (3) matched/monitored by camera (12),
    (d4) patient/user must ingest all medication as monitored by camera (12);
(e) transparent straw (11)
    (e1) straw (11) length to insure patient/user "on camera" (13),
    (e2) facial recognition match controlled by CPU (13) to confirm/record user ID,
    (e3) camera (13) views/records medication being ingested through straw for color match,
    (e4) camera (13) views/records patient talking to confirm medication has been swallowed;
(f) camera (12) views/records medication in cup to confirm all medication has been drawn into straw (11).

Figure 3:
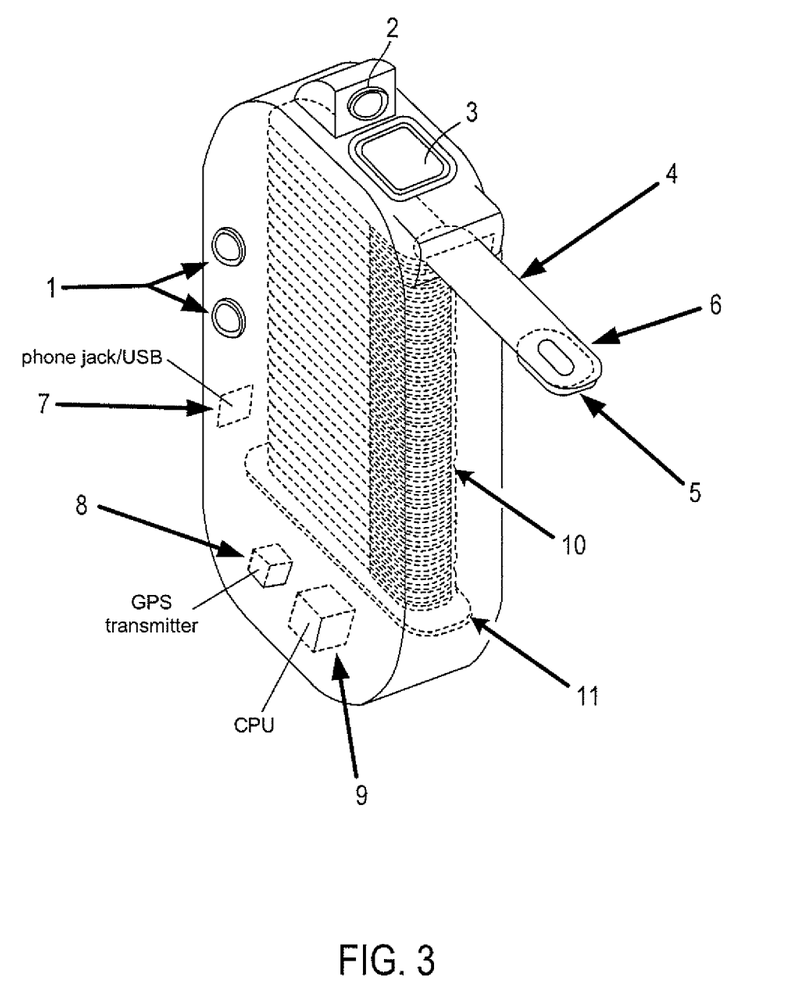
FIG. 3 is a perspective view of the ODF (orally dissolving film) dispensing device.

FIG. 3 shows the ODF (orally dissolving film) version of the drug-dispensing device. The ODF version has connectivity to the web and to the server-based management system through phone jack/USB or WiFi (7). A patient/user initially receives the device, loaded with medication, from a pharmacy where he or she would provide his or her address (where the device will be used), a scan of his or her thumbprint, and a photo. Upon reaching his or her home, the patient/user initializes the device for operation by first plugging in to a live phone jack or connecting to a web connected computer through USB or by connecting to his or her WiFi network and connecting to the managing web-based server (this connection is confirmed by blinking green alert/alarm lights (1). This confirms the location of the device through use of the onboard GPS transmitter (8) (positive GPS match will be confirmed by blinking green alert/alarm lights (1), the patient/user then places a thumb on the thumb print reader (3) to authenticate his or her ID (the reader compares thumbprint with the scan taken at pharmacy), positive ID is confirmed with blinking green alert/alarm lights (1) and starts the clock on the prescription instructions loaded onto the device CPU (9) at the pharmacy.

The CPU (9) monitors the prescription instructions loaded and alerts patient/user of next available dose with blinking alert/alarm lights (1). To initiate the dispensing of that dose, the patient/user first places a thumb on the thumb print reader (3) to authenticate his or her ID which will return blinking green alert/alarm lights (1) if ID is confirmed and if GPS transmitter (8) data matches patient/user home address. Again, given matching ID and location data, the device allows one ODF stick (4) to extend from the device. The medication (5) is located on the underside of the stick (4) and a unique stick ID is placed under a rapidly dissolving opaque film (6). The ODF stick (4) is measured to insure the patient/user is well within the frame of the camera (2). The patient/user holds the device up to his or her face and places the end of the ODF stick (4) into his or her mouth so that the medication (5) rests on his or her tongue. While the ODF stick (4) is in the user/patient's mouth, the camera (2) views and records the event. When the ODF medication (5) and upper opaque film (6) have completely dissolved (less than 30 seconds), the patient/user removes the ODF stick (4) from his or her mouth to confirm ingestion of medicine (as seen through the transparent ODF stick (4) and to view record the unique ODF stick ID revealed after the opaque film (6) on the upper side of the ODF stick (4) has dissolved. Medication (5) can contain dye and the color is coded into the ID hidden by the opaque film (6), this color code is compared to the color left on the patient/user's tongue after the medication (5) has dissolved. The ODF sticks are stacked (10) horizontally inside the device and are fed upward to be dispensed by a spring-loaded platform (11). When user/patient has completed the dosing cycle, they pull the ODF stick (4) free of the device to start the clock for the next dose.

Figure 4:
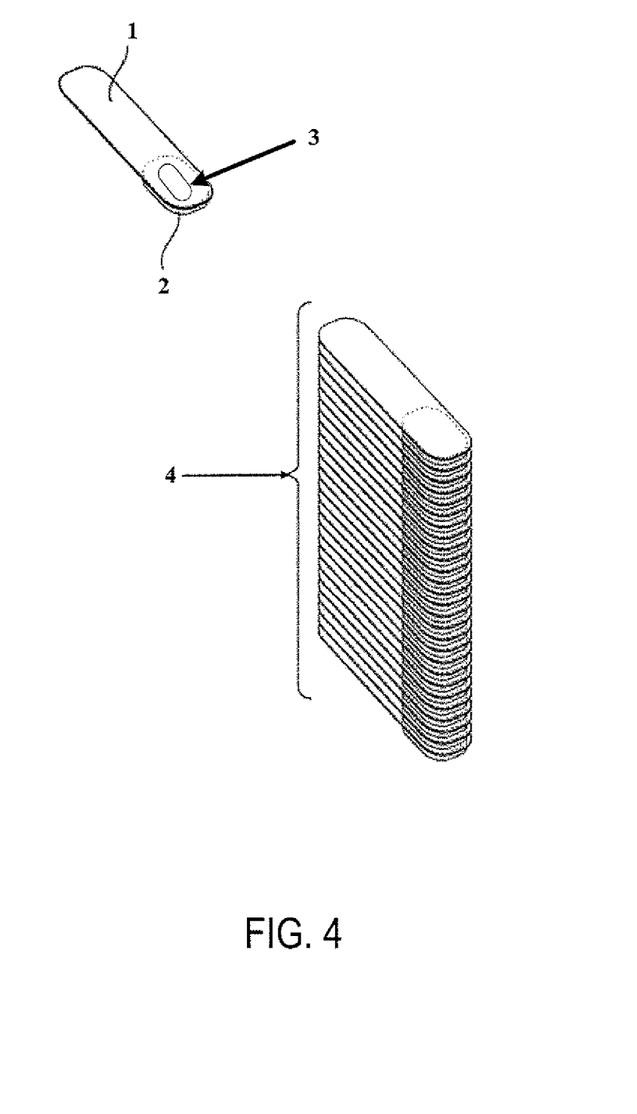
FIG. 4 is a perspective view of the ODF dosing sticks stacked in the device.

FIG. 4 depicts a single ODF stick (1) and a view of stacked ODF sticks (4) as they would appear within a device. Each ODF stick (1), including thin film medication (2) and opaque film (3) measures less than 1.5 mm. A 30-day supply of medication, or 90 doses, when stacked as shown, measures less than 6 inches in height.

Figure 5:
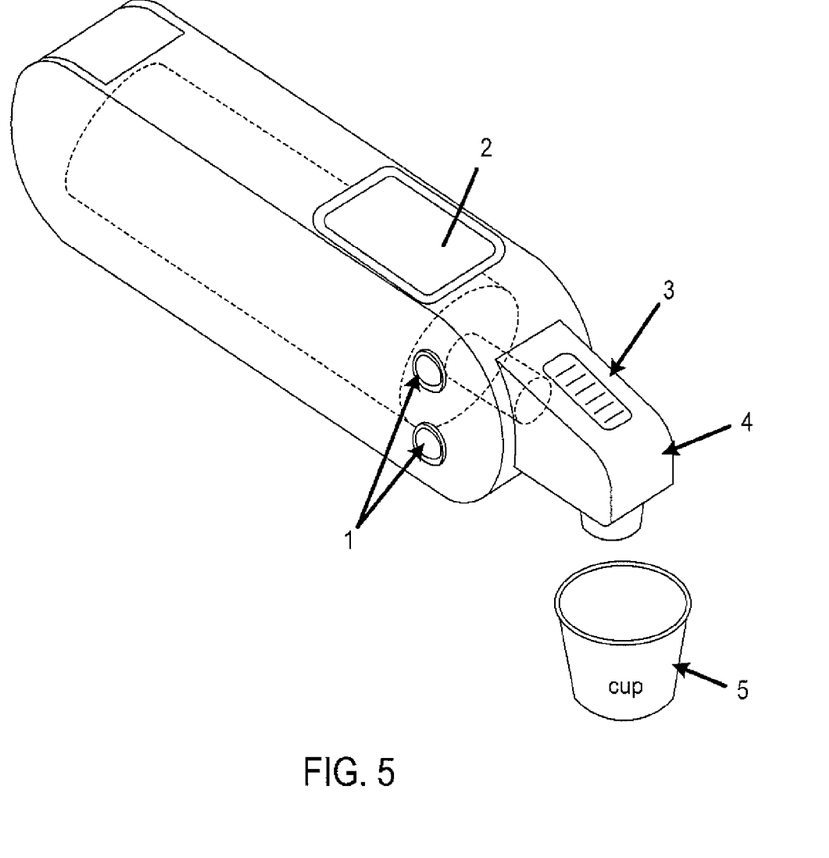
FIG. 5 is a non-monitored liquid medication dispensing device.

FIG. 5 depicts a version of the device meant for low-risk user/patients. This version does not include GPS tracking or video monitoring, but does provide security against use by anyone other than the user/patient. This version of the device requires user authentication through use of a thumb print reader (2). In use, the patient/user would initiate dispensing a dose by first placing his or her thumb on the thumb print reader (2). With positive ID, the alert/alarm lights (1) flashes green and liquid medication is released into the medication dispenser where the patient/user can verify the dose through a sight glass (3) and, finally, dispenses the dose into a cup (5) with a final placement of his or her thumb on the thumb print reader (2).

Figure 6:
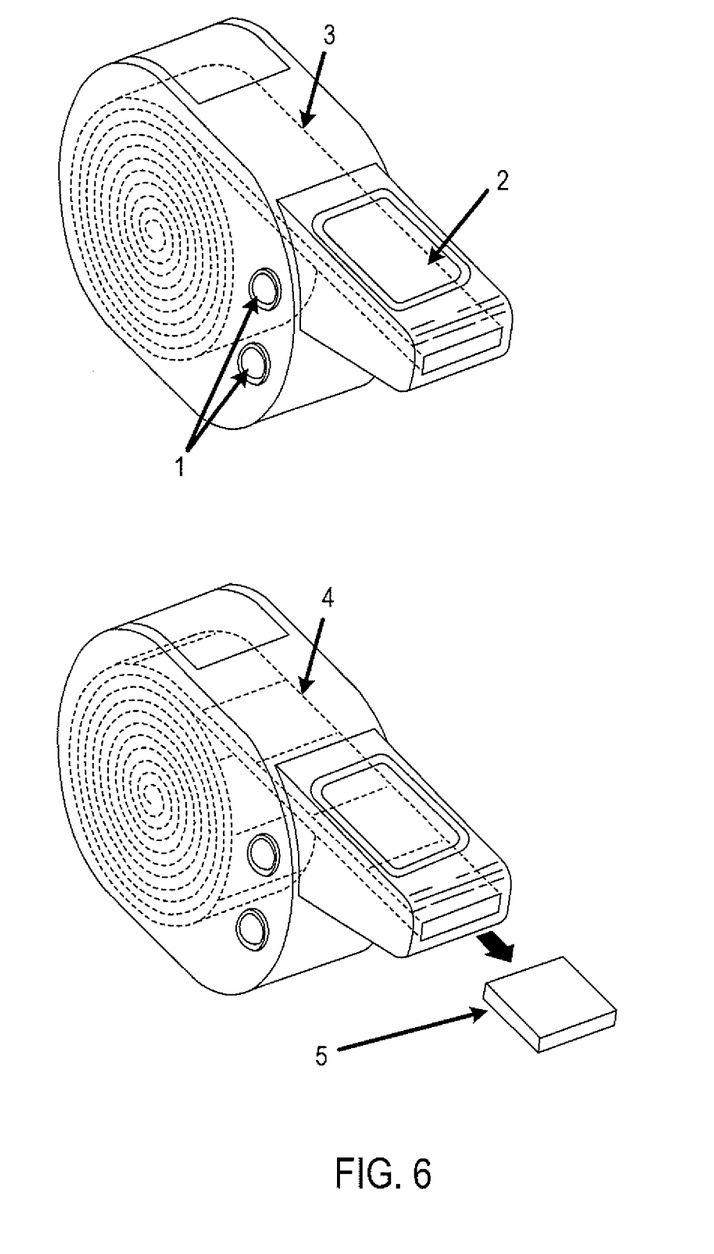
FIG. 6. is a non-monitored thin film dispensing device.

FIG. 6 shows a "low risk" version of the ODF (thin film) device. As with the low risk version of the liquid medication dispenser, there is no GPS or video monitoring built into this device. A patient/user initiates the dispensing cycle by placing his or her thumb on the thumb print reader (2) and positive ID is confirmed by green flashing Alarm/Alert lights (1). Patient/user then pulls a dose (5) free from the perforated roll (4) of thin film medication.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A drug dispenser comprising:
   a housing;
   alarm/alert lights that blink in different colors to provide indications to a user;
   a thumbprint reader to authenticate the user;
   a dispenser bay that accommodates a cup that allows a user to ingest medicine through a transparent straw;
   an onboard camera for recording ingestion of medicine.

* * * * *